(12) United States Patent
Florent et al.

(10) Patent No.: US 10,646,184 B2
(45) Date of Patent: May 12, 2020

(54) AUTOMATIC ROAD MAPPING FOR HEART VALVE REPLACEMENT

(75) Inventors: Raoul Florent, Ville Davray (FR); Nicolaas Hylke Bakker, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1288 days.

(21) Appl. No.: 13/133,693

(22) PCT Filed: Dec. 7, 2009

(86) PCT No.: PCT/IB2009/055547
§ 371 (c)(1),
(2), (4) Date: Jun. 9, 2011

(87) PCT Pub. No.: WO2010/067300
PCT Pub. Date: Jun. 17, 2010

(65) Prior Publication Data
US 2011/0249794 A1    Oct. 13, 2011

(30) Foreign Application Priority Data
Dec. 12, 2008    (EP) .................................... 08305929

(51) Int. Cl.
*A61B 6/00*    (2006.01)
*A61B 6/12*    (2006.01)
(Continued)

(52) U.S. Cl.
CPC ................ *A61B 6/504* (2013.01); *A61B 6/12* (2013.01); *A61B 6/463* (2013.01); *A61B 6/481* (2013.01);
(Continued)

(58) Field of Classification Search
CPC .... A61B 2017/00243; A61B 2034/105; A61B 2090/376; A61B 6/12; A61B 6/463;
(Continued)

(56) References Cited

U.S. PATENT DOCUMENTS 4,444,196 A * 4/1984 Stein ............................. 600/431
5,734,739 A    3/1998 Sheehan et al.
(Continued)

FOREIGN PATENT DOCUMENTS

WO    2007080569 A2    7/2007
WO    2008104921 A2    9/2008
(Continued)

OTHER PUBLICATIONS

By J. Garcia, "On-Line Multi-Slice Computed Tomography Interactive Overlay With Conventional X-Ray: A New and Advance Imaging Fusion Concept" International Journal of Cardiology; Elsevier Science Publishers, Amsterdam, Netherlands, vol. 133, No. 3, Apr. 17, 2009; pp. E101-E105.

*Primary Examiner* — Amelie R Davis

(57) ABSTRACT

The present invention relates to a method for automatic road mapping for heart valve replacement and an examination apparatus for automatic road mapping for heart valve replacement. In order to provide the cardiologist or surgeon with better information during PHV implantation, an examination apparatus for automatic roadmapping for heart valve replacement is provided, that comprises at least one X-ray image acquisition device (10), a calculation unit (18) and a display device (20). The image acquisition device is adapted to acquire (32) at least one X-ray image of a vessel root region of a heart with injected contrast agent and to acquire (46) at least one current fluoroscopy image of the vessel root region with a replacement valve inserted into the vessel. The calculation unit is adapted to identify (34) vessel information data within the at least one acquired image, to model (Continued)

(36) vessel root representation using the vessel information data and to generate (44) a composite image by a combination of the model of the vessel root representation with the at least one fluoroscopy image. The display unit is adapted to display (48) the composite image.

18 Claims, 6 Drawing Sheets

(51) Int. Cl.
| | | |
|---|---|---|
| *G06T 7/00* | (2017.01) | |
| *A61B 17/00* | (2006.01) | |
| *A61F 2/24* | (2006.01) | |
| *A61B 90/00* | (2016.01) | |
| *A61B 34/10* | (2016.01) | |

(52) U.S. Cl.
CPC .......... *A61B 6/5235* (2013.01); *G06T 7/0012* (2013.01); *A61B 6/503* (2013.01); *A61B 2017/00243* (2013.01); *A61B 2034/105* (2016.02); *A61B 2090/376* (2016.02); *A61F 2/24* (2013.01); *G06T 2207/10116* (2013.01); *G06T 2207/10121* (2013.01); *G06T 2207/20212* (2013.01); *G06T 2207/30048* (2013.01); *G06T 2207/30101* (2013.01)

(58) Field of Classification Search
CPC ......... A61B 6/481; A61B 6/503; A61B 6/504; A61B 6/5235; A61F 2/24; G06T 2207/10116; G06T 2207/10121; G06T 2207/20212; G06T 2207/30048; G06T 2207/30101; G06T 7/0012

USPC ........................................................ 600/431
See application file for complete search history.

(56) References Cited

U.S. PATENT DOCUMENTS

| | | |
|---|---|---|
| 6,711,433 B1 | 3/2004 | Geiger et al. |
| 6,782,284 B1 | 8/2004 | Subramanyan et al. |
| 7,333,643 B2 | 2/2008 | Murphy |
| 7,435,257 B2 | 10/2008 | Lashinski |
| 2004/0225331 A1 | 11/2004 | Okerlund et al. |
| 2006/0079759 A1* | 4/2006 | Vaillant et al. ............... 600/424 |
| 2006/0267977 A1 | 11/2006 | Barfuss et al. |
| 2007/0016108 A1 | 1/2007 | Camus et al. |
| 2007/0055148 A1* | 3/2007 | Klingenbeck-Regn ..................... A61B 6/504 600/431 |
| 2007/0288000 A1* | 12/2007 | Bonan ................... A61B 6/481 606/46 |
| 2008/0085042 A1 | 4/2008 | Trofimov |
| 2008/0234576 A1 | 9/2008 | Gavit-Houdant |
| 2008/0267490 A1 | 10/2008 | Gorges |
| 2008/0273799 A1* | 11/2008 | Kimura ........................ 382/200 |
| 2009/0082660 A1* | 3/2009 | Rahn ........................ G06T 7/12 600/411 |
| 2009/0123050 A1* | 5/2009 | Ionasec ................... G06K 9/00 382/131 |
| 2009/0220050 A1* | 9/2009 | Guhring ................ A61B 5/055 378/98.5 |
| 2009/0306500 A1 | 12/2009 | Rahn et al. |

FOREIGN PATENT DOCUMENTS

| | | |
|---|---|---|
| WO | 2008107814 A1 | 9/2008 |
| WO | 2009144697 A1 | 12/2009 |

\* cited by examiner

AUTOMATIC ROAD MAPPING FOR HEART VALVE REPLACEMENT

FIELD OF THE INVENTION

The present invention is related to a method for automatic road mapping for heart valve replacement and an examination apparatus for automatic road mapping for heart valve replacement amongst others.

BACKGROUND OF THE INVENTION

Treatment of heart valve problems or heart valve diseases is becoming more important because of an ageing population. Such diseases, for example aortic stenoses, usually require the replacement of a native heart valve, for example of the aortic valve, which is the most important and thus most critical valve of the human heart. The valve replacement can be done in two different ways, for example. The surgical valve replacement is considered as a "gold standard" treatment. As an alternative, the so-called percutaneous valve replacement is a fairly new intervention that is increasingly applied. Percutaneous valve replacement usually includes transcatheter heart valve implantation. With this method the valve can be placed either through the femoral vessels, vein or arteria (transfemoral) or through the apex of the left ventricle (transapical). Three main basic techniques for percutaneous heart valve (PHV) implantation do exist. First to be mentioned is the antegrade transseptal approach, second the retrograde approach and third the transapical approach. In all these approaches, one of the most critical points is the precise positioning of the usually implantable valve device under fluoroscopy imaging prior to deployment. In particular, the valve should be correctly positioned in line with a native valve commissure and the aortic annulus. To achieve this positioning, a super-aortic angiography (with contrast agent) is performed in order to determine the optimal projection for PHV deployment, showing the annulus profile. For example, a frame is manually selected, stored and subsequently used as pre-implant reference image. For a correct positioning of the valve it is necessary to supply the cardiologist or cardiac surgeon with information about the vessel structure. In Percutaneous Coronary Interventions (PCI), it is known that the cardiologist can be provided with so-called cardiac road mapping. This cardiac road mapping provides the operator with the information about the accurate coronary localization, see, for example, WO 2008/104921 A2. But still, one of the main difficulties the staff carrying out the operation faces during PHV implantation is the accurate positioning of the prosthesis. The manually acquired reference image is only of certain support, because the cardiologist or cardiac surgeon has to connect the information from the reference image with fluoroscopy images taken live during the operation procedure using his imagination. It has shown that this mental process is prone to error and makes the positioning a delicate and tiring operation.

SUMMARY OF THE INVENTION

The present invention aims at providing the cardiologist or surgeon with better information during percutaneous heart valve implantation.

The object is reached with an examination apparatus for automatic road mapping for heart valve replacement and a method for automatic road mapping heart valve replacement, according to the independent claims.

In an exemplary embodiment, a method is provided that comprises the following steps. First, at least one image of the vessel root region, e.g. aortic root or pulmonary root region, is acquired with injected contrast agent. Then vessel information data within the at least one acquired image is identified. Further, a vessel root representation is modelled using the vessel information data. Then at least one current fluoroscopy image of the vessel root region is acquired. By combining the at least one fluoroscopy image with the model of the vessel root representation, the composite image is then generated. Next, the composite image is displayed on a display.

By these steps it is possible to provide an operator, i.e. a cardiologist or cardiac surgeon, for example, with the information that is necessary for a correct placement of the artificial valve to be implanted. The composite image displays the current situation in form a of greyscale fluoroscopy image in relation to the vessel root representation. The location and orientation of the artificial valve can be seen on this fluoroscopy image due to the frame parts of the artificial valve that provide enough contrast for the X-ray image. The relation to the vessel root, and of course also to the valve annulus, can easily be captured from the model of the vessel root representation that is combined with the fluoroscopy image. Hence, the user can adjust the positioning of the replacement valve for example through a catheter device, i.e. the user can adjust the angle and depth in respect to the annulus. The model of the vessel root representation is in a way a sort of manipulated image data; that means the model stands for a higher level of information. Combining the model with the fluoroscopy image has the advantage that as little information of the fluoroscopy image as necessary is covered or erased by the additional image data during the composition, as all details on the fluoro image are important for the user. In other words, the composite image is a sort of hybrid image composed of fluoroscopy image data and an abstract model image data of the vessel root representation. No shading or covering of the fluoroscopy image takes place. The vessel image with the injected contrast agent is usually a pre-implant baseline vessel-graphy. But for a better control, the replacement valve can be roughly positioned before the contrast agent is injected. Here, the device can then also be seen on the image. As a result of the method, a vessel root model is shown in a fluoroscopy image on the display. In other words, the inventive method can easily be detected by its result.

Although, at the moment the focus in heart valve treatment lies on the aortic valves, the present invention is also related to the replacement of other types of heart valves, such as pulmonary, mitral and tricuspid valves. The pulmonary valve is rather similar to the aortic valve in that it links a ventricle (right) to a main artery (pulmonary). Therefore the following description of the invention is focussed on the aortic valve, but the same can be applied to the pulmonary valve. The other two valves are atrio-ventricular valves (linking one atrium (left or right) to the ventricle on the same side (left or right). The mitral valve (on the left side) is also very important. However, the inventive model always amounts to produce a simplified structure of the valve's surrounding anatomy as displayed in a CA-filled sequence, and the composite image principle remains the same.

Hence, in the following the term aortic root region may be used for vessel root region. It is to be noted that this term is also understood as valve-vicinity. Further, the term vessel information data may be used for vessel information data or valve-vicinity data and the term aortic root representation may stand for vessel root representation or valve-vicinity representation. Although the invention will be described using the narrow term "aorta", the scope of the invention covers all type of heart valves as well. That is, the invention is also related to (and thus applicable) to atrio-ventricular valves (mitral, tricuspid) that link two chambers and not one chamber to one vessel. Hence, the term valve-vicinity covers all four cardiac valves.

It is further to be noted that the roadmapping process can be achieved with hardly any manual intervention. In particular, in a preferred embodiment, no region-of-interest placement, and no clicking process designating the aortic root is involved.

In a preferred exemplary embodiment, the vessel root outline is detected in the at least one acquired image as vessel information data.

The outline of the aorta root, i.e. the vessel root, has the advantage that it can easily be combined with other image data without covering or erasing too much information within this other image data. On the other hand, the outline still provides the surgeon with enough information for a correct positioning of the artificial valve to be deployed. The outline detection can be achieved by using medial-axis transforms or similar techniques.

In another preferred exemplary embodiment, the vessel root region is segmented from the acquired image as vessel information data.

The segmentation of the vessel root region is an alternative or complementary step for providing vessel information data. The segmentation can be applied to the full vessel root region. This can be achieved through purely region based techniques or the formable contour approaches, etc. The advantage is that the surgeon can be provided with additional information about the vessel situation in direct relation to the artificial valve or implant device. The segmentation can be achieved through purely region-based techniques or deformable contour approaches, etc.

In another preferred exemplary embodiment of the invention, a sequence of images of the vessel root region is acquired with injected contrast agent and the image with the best contrast is selected for the step of identifying the vessel information data.

This enables an improved modelling of the vessel or aortic root representation because the image data used for identifying the vessel or aortic information data provides more information when the contrast is better compared to an image with a low contrast. The selection can automatically be performed be filtering techniques and temporal histogram analysis, for example.

In another preferred embodiment, the background in the at least one image is estimated and subtracted from the image before identifying the vessel information data.

By subtracting the background from the image, an image is achieved with data information focused on the step of identifying the vessel or aortic information data. In other words, the image used for further steps is reduced to the only information actually needed, which also improves the modelling step for achieving a vessel root representation.

In a further embodiment, pre-operative data, like the segmentation of the aortic root in a CT volume for example, could be used to help the detection of the segmentation of the vessel outline in the angiographic image. This can be applied alternatively or in addition to the DSA described above.

In a preferred embodiment, a so-called non-intrusive model is generated, or produced respectively, for the implantation area.

That means, a model is generated where the area of special interest, i.e. the area where the implant will be located, is reduced to only the basic information, or even better where no information is shown in that area to allow for a better view of the implant.

In a further preferred embodiment, the aortic root representation, i.e. the model of the vessel root, is used for measuring, checking and rating purposes.

Hence, the model is not only used for generating a composite image but also used for other purposes supporting the cardiologist or cardiac surgeon. This may also include automatic geometric measurements, such as annulus dimensions, leaflet plane orientations, etc, that can be stored for further purposes, such as controlling examinations at a later time or even adjusting or adapting the replacement valve device.

According to the invention, in an exemplary embodiment, the object is also reached with an examination apparatus for automatic road mapping for heart valve replacement that comprises at least one X-ray image acquisition device, a calculation unit and a display device. The image acquisition device is adapted to acquire at least one X-ray image of the vessel root region of a heart with injected contrast agent and to acquire at least one current fluoroscopy image of the vessel root region with a replacement valve inserted into the aorta. The calculation unit is adapted to identify vessel information data within the at least one acquired image, to model vessel root representation using the vessel information data and to generate a composite image by a combination of the model of the vessel root representation with the at least one fluoroscopy image. The display unit is adapted to display the composite image.

The examination apparatus, according to the invention, supplies the surgeon or cardiologist with improved information concerning the exact positioning of the artificial heart valve. The information in form of a composite image can easily be received by the surgeon and easily understood because the relation of the artificial valve and the vessel root region, e.g. the aortic root region, can be extracted directly from the image. In fact, additional abstracting mental processes by the surgeon are not necessary. Hence, the examination apparatus facilitates the heart valve replacement operation. Anyway, the inventive apparatus can easily be detected, because as a result a fluoroscopy image is displayed that also shows a vessel root model.

The invention also provides an X-ray imaging system with an examination apparatus according to the above mentioned embodiment and according to the embodiment defined by a claim.

Thus, a system can be provided that serves for other examinations purposes as well as being specifically adapted for the heart valve replacement procedure itself. For example, the imaging system also includes a resting surface for the object to be examined.

The invention also relates to a catheterization laboratory system with an examination apparatus according to the invention.

According to another exemplary embodiment of the present invention, a computer readable medium is provided, in which a computer program for automatic road mapping for heart valve replacement is stored which, when being executed by a processor, causes the processor to carry out the above mentioned method steps.

Furthermore, according to another exemplary embodiment of the present invention, a computer program element for automatic road mapping for heart valve replacement is provided which, when being executed by a processor, causes the processor to carry out the above mentioned method steps.

Those skilled in the art will readily appreciate that the method of automatic road mapping for heart valve replacement according to the invention may be embodied as a computer program, i.e. by software, or may be embodied using one or more special electronic optimization circuits, i.e. in hardware, or the method may be embodied in hybrid form, i.e. by means of software components and hardware components.

This exemplary embodiment of the invention covers both a computer program that right from the beginning uses the invention and a computer program that by means of an update turns an existing program into a program that uses the invention.

Further on, the computer program element might be able to provide all necessary steps to fulfil the procedure of the method as described above.

According to a further exemplary embodiment of the present invention, a medium for making a computer program element available for downloading is provided, which computer program element is arranged to perform the method according to one of the previously described embodiments of the invention.

For example, existing imaging systems can be upgraded with a new software, which, when being executed by a processor, causes the system to carry out the above mentioned method steps.

These and other aspects of the invention will be apparent from the exemplary embodiments described hereinafter with reference to the drawings.

DETAILED DESCRIPTION OF EMBODIMENTS

In the following, the invention is exemplarily described in relation with the replacement of the aortic valve. But the invention is also focussed on the replacement of other types of heart valves, such as pulmonary, mitral and tricuspid valves. Hence, in the following the term aortic root region is used instead of vessel root region or valve vicinity (area surrounding the annulus that is visible after contrast injection; this can be a vessel root (aortic, pulmonary), and/or the annulus walls on the surface of one or two cardiac chambers), the term aortic information data instead of vessel information data and the term aortic root representation also stands for vessel root representation. Anyway, it is clear that the scope of the invention covers other type of heart valves as well.

Figure 6:
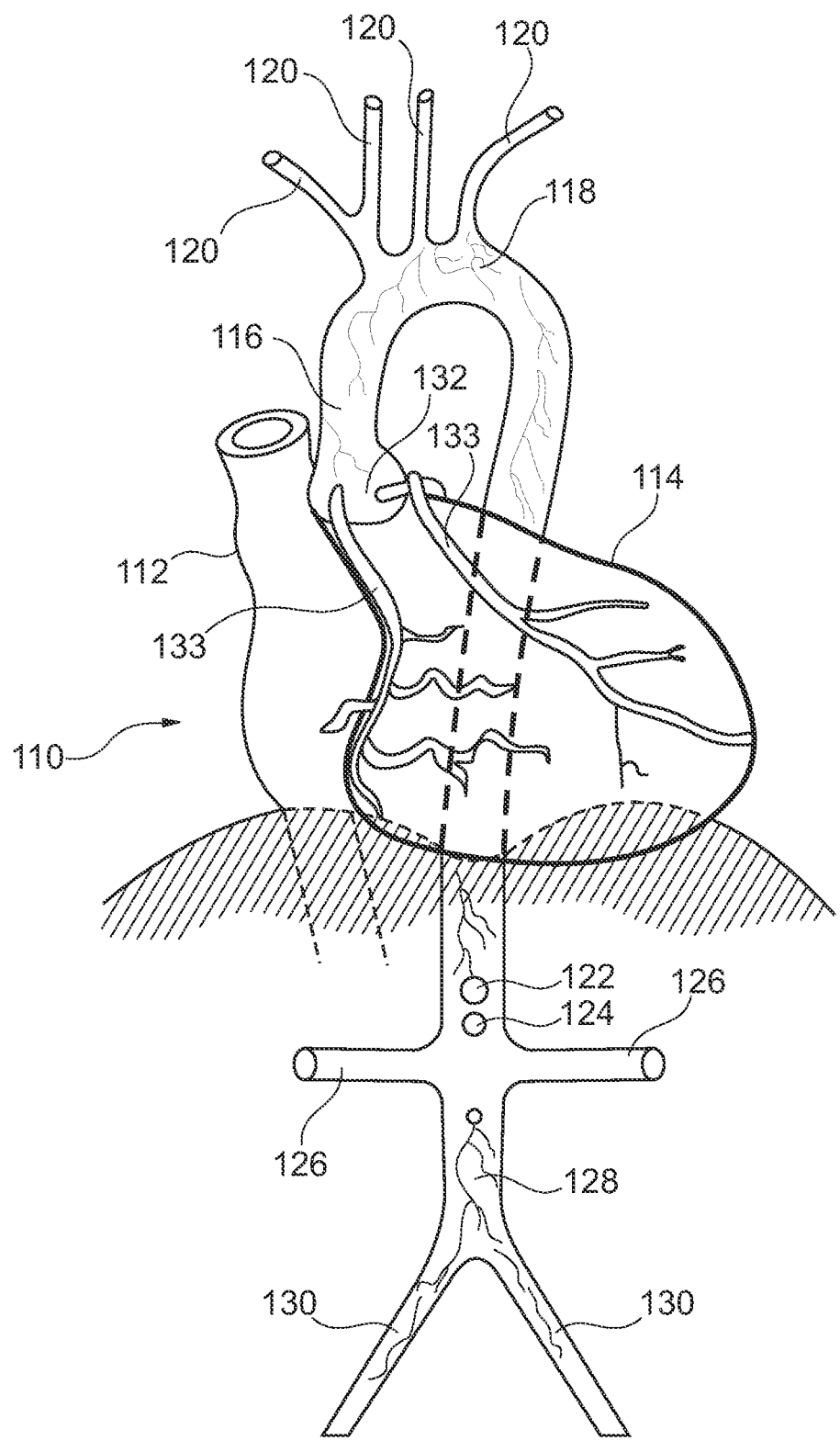
FIG. 6 schematically shows the structure of the aorta.

In FIG. 6, heart 110 is shown with a right part 112 and a left part 114 in relation to the main vessels. The right part 112 is placed on the vena cava in the diagram. It should designate the part of the heart irrigated by the right coronary. On top of the left part an ascending aorta 116 can be seen. The ascending aorta 116 is forming an arch 118 where several other vessels 120 are connected to the aorta 116. The aorta 116 then leads downwards where several further vessels are connected, such as the celiac artery 122 and the superior mesenteric artery. Still further, the aorta splits up into the renal arteries 126 and the inferior mesenteric artery 128 that leads to the iliac arteries 130. This part is also called the abdominal aorta. The connection point to the heart itself, so to speak the starting point of the aorta 116, is the root 132. Further, two coronary arteries 133 are connected in the root region 130. An aortic heart valve (not shown) is located at the root 132.

Figure 7:
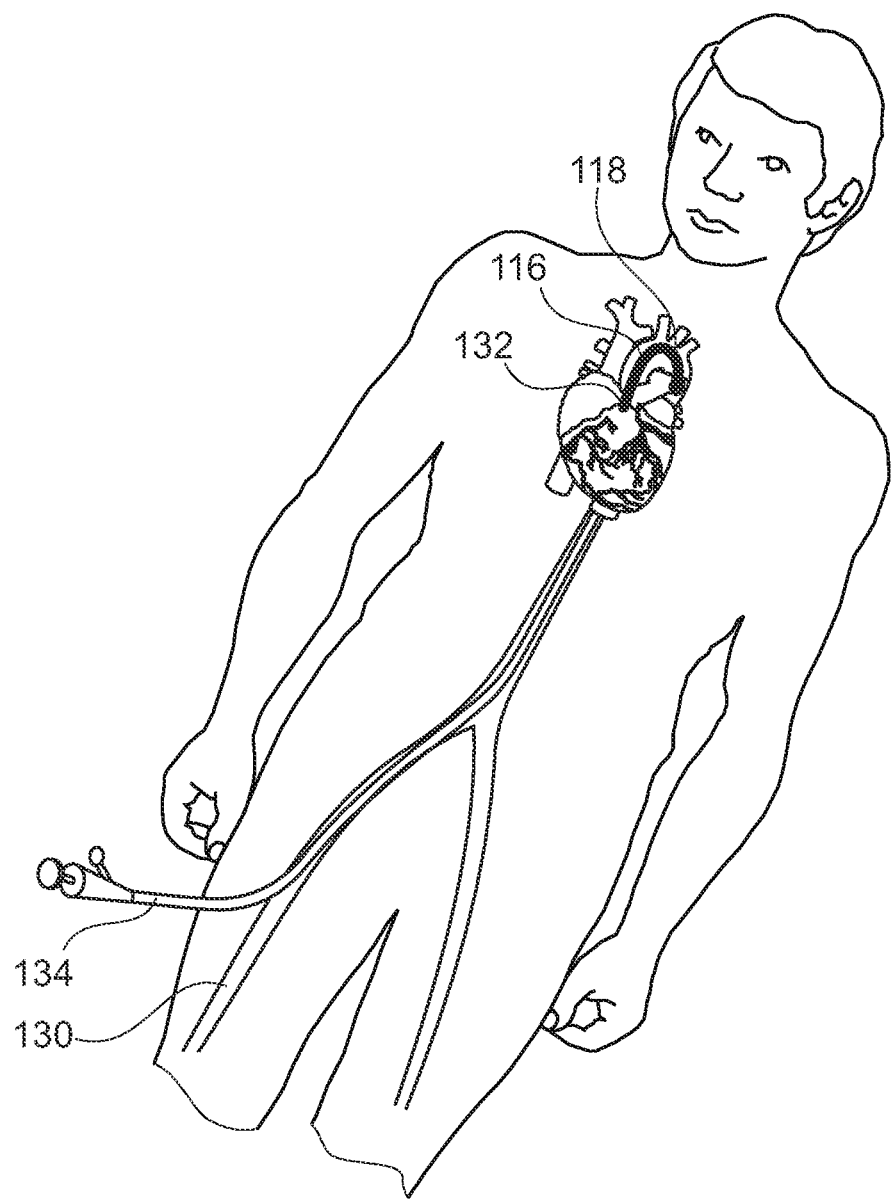
FIG. 7 schematically shows a catheterization of an object for a valve replacement.

For a heart valve replacement such as the replacement of the aorta valve located at the root 132, in FIG. 7 valve delivery catheter 134 is inserted in the groin into one of the iliac arteries 130 and threaded up to the heart valve to be replaced (see FIG. 7). In other words, the catheter 134 follows the aorta passing the arch 118 until it reaches the root region where the valve is deployed after correct positioning.

Figure 1:
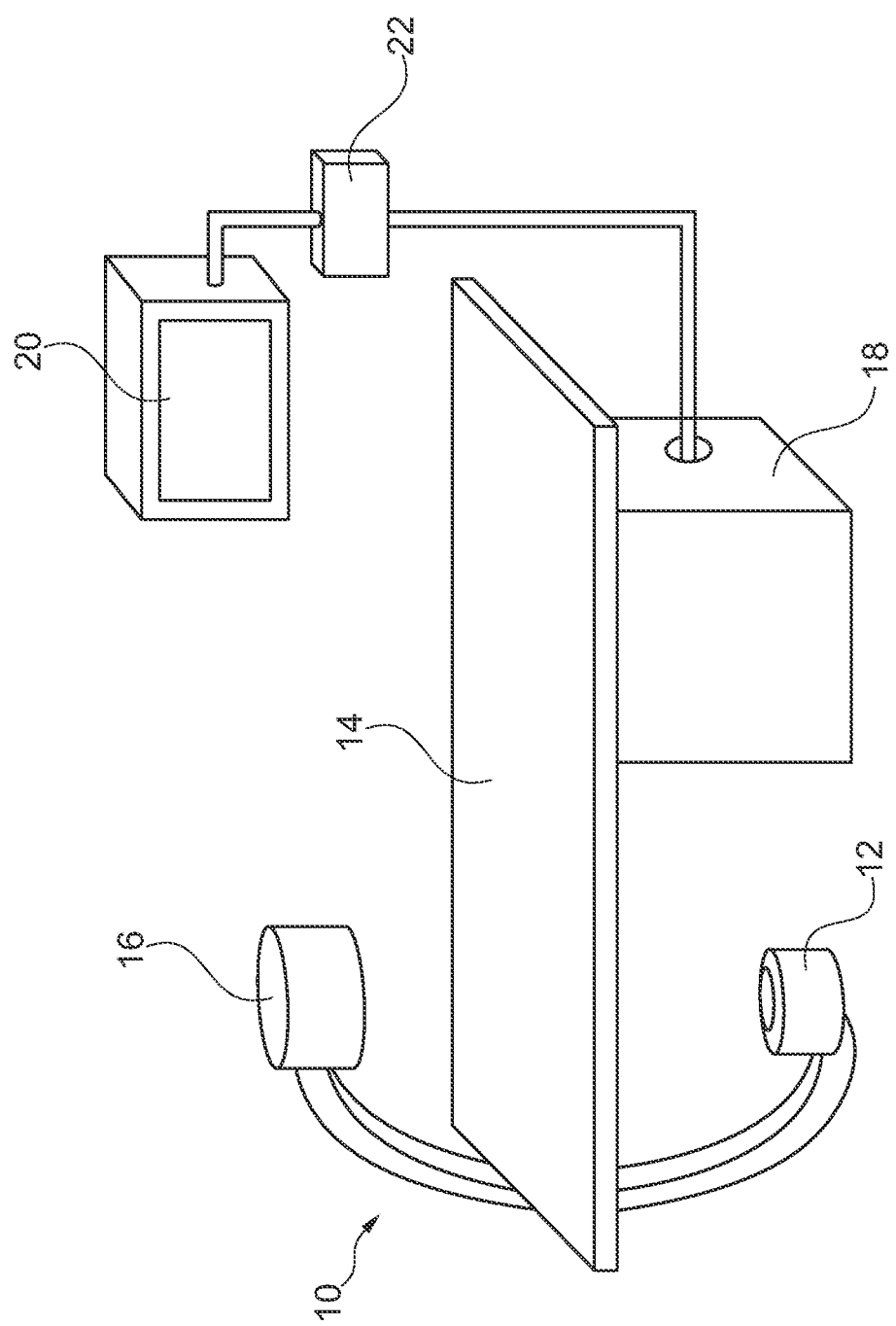
FIG. 1 shows an X-ray imaging system for the use in a catheterization laboratory.

FIG. 1 schematically shows an X-ray imaging system 10 for the use in a catheterization laboratory with an examination apparatus for automatic roadmapping for heart valve replacement. The examination apparatus comprises an X-ray image acquisition device with a source of X-ray radiation 12 provided to generate X-ray radiation. A table 14 is provided to receive a subject to be examined. Further, an X-ray image detection module 16 is located opposite the source of X-ray radiation 12, i.e. during the radiation procedure, the subject is located between the source of X-ray radiation 12 and the detection module 16. The latter is sending data to a data processing unit or calculation unit 18, which is connected to both the detection module 16 and the radiation source 12. The calculation unit 18 is located underneath the table 14 to save space within the catheterization laboratory. Of course, it could also be located at a different place, such as a different room. Furthermore a display device 20 is arranged in the vicinity of the table 14 to display information to the person operating the X-ray imaging system, i.e. a clinician such as a cardiologist or cardiac surgeon. Preferably the display device 20 is movably mounted to allow for an individual adjustment depending on the examination situation. Also, an interface unit 22 is arranged to input information by the user. Basically, the image detection module 16 generates images by exposing the subject to X-ray radiation, wherein said images are further processed in the data processing unit 18. It is noted that the example shown is of a so-called C-type X-ray image acquisition device. Of course, the invention also relates to other types of X-ray image acquisition devices. The procedure according to the invention is described in more detail below.

Figure 2:
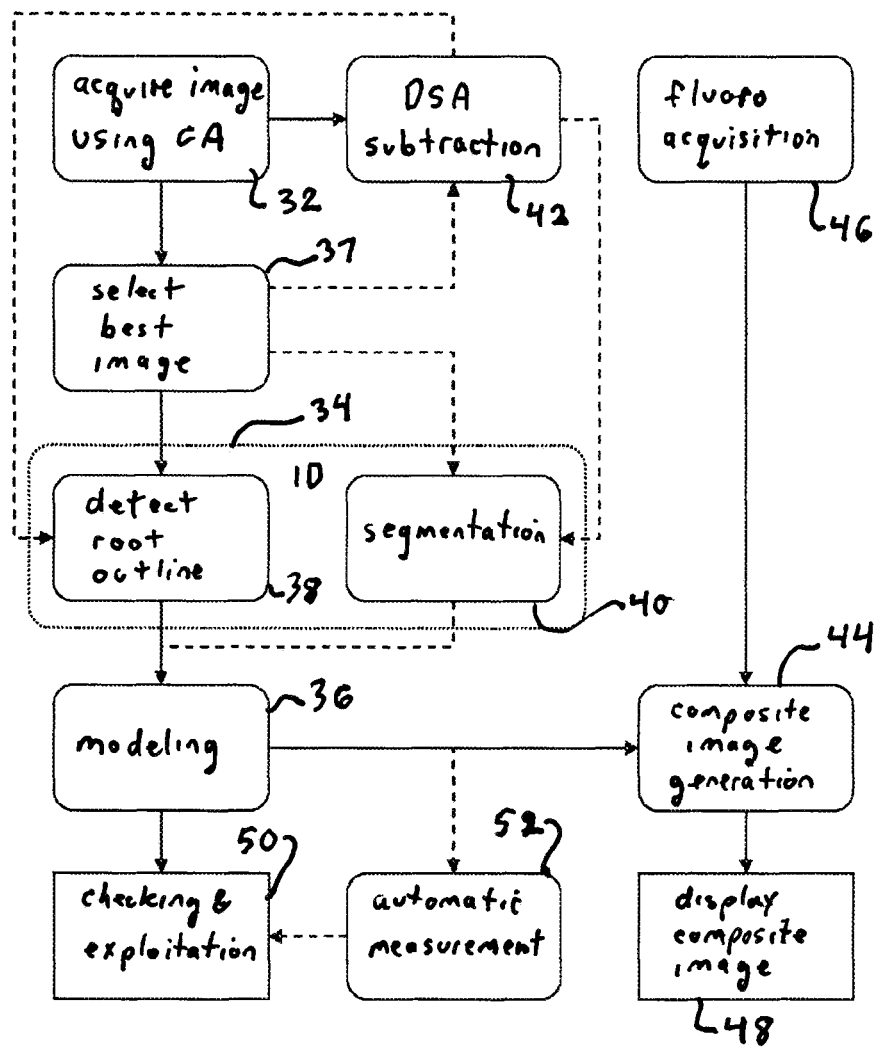
FIG. 2 schematically describes the method steps according to the invention.

FIG. 2 schematically shows a flowchart of the steps, according to the invention. In a first step 32 an aortogram is acquired. Usually, an aortogram consists of a sequence of images that are taken by an X-ray imaging device of an object of interest which in the case of an aortogram is of course the aorta itself. These images are acquired after a contrast agent (CA) is injected into the aorta in order to make the volume of the aorta visible in an X-ray image. Of course, the aorta can be seen in an X-ray image without a contrast agent, but the contrast agent provides a better visual detectability of the aorta. Instead of a sequence of images for an aortogram, it is also possible to acquire only one image of the aorta root region with injected contrast agent.

According to the invention, the term aortogram stands for a sequence with a contrast agent injected into a vessel (or heart chamber) to visualize an anatomic location or surrounding of a valve heart. Instead of aortogram, the terms vesselgram or angiogram can also be used. Another proposed term is valvologram that is also suitable for the description of the above mentioned sequence of images concerning valves of the heart.

After acquiring at least one image in the acquisition step 32, in an identification step 34 aortic information data is identified within the at least one acquired image. The aortic information data is then used for modelling an aortic root representation in a modelling step 36.

In order to achieve the aortic root representation in further steps, the aortogram image or images can be refined before modelling the aortic root representation. For example, after the aortogram acquisition 32, an image with the best contrast for identifying aortic information data is selected in a selection step 37. The selected image with the best contrast is then used in the identifying step 34.

Preferably in a detection step 38 the aortic root outline is detected in the selected image. Alternatively, or additionally, the selected image is used in a segmentation step 40 where the aortic root region is segmented from the acquired image as the aortic information data.

For an improved image data that is used in the further steps, the aortogram is processed in a subtraction step 42 where a background is estimated in the at least one image or the image sequence and a digital subtraction angiogram (DSA) is performed for subtracting the background from the image before using the image data in the identifying step 34. The DSA image can be used in the detection step 38 for detecting the root outline and for the segmentation step 40 for segmenting the root region.

For further improved image data quality it is also possible to use a selected image with a best contrast resulting from the selection step 34 in the background estimation and DSA performing step 42 for further processing.

The result of the identification step 34, i.e. the root outline and/or the root region, is then used in the modelling step 36. In this step 36 the aortic information data is used for modelling the aortic root representation.

The aortic root representation is basically consisting of image data representing a model of the aorta itself. In a preferred embodiment, the aortic root representation comprises an annulus model, i.e. the annulus plane of the aorta. For example, the model can comprise curve definitions and/or vector data. In other words, the model represents a far more enhanced image data than only image pixels as is the case in the acquired image at the beginning. So to speak, the aortic root representation is image information on a higher level than the acquired pixel image from the aortogram at the beginning. The aortic root representation is then used in a composite image generating step 44 where the composite image is generated.

The aortogram acquisition 32 and the further processing steps are usually achieved before placing the replacement valve at its location at the aorta root. During the procedure of inserting the artificial valve into the aorta or into any other vessel in order to be able to place it at its position at the heart valve to be replaced, fluoroscopy images are acquired in a fluoro acquisition step 46. These X-ray images show the replacement valve due to the frame parts used in the replacement valve. When using, for example, material from pigs or bovine/ovine for the valve leaflets, these cannot be seen in the fluoro image. But the detectable frame construction gives enough information for the location and orientation of the replacement valve.

In the composition step 44 the fluoro images resulting from the acquisition step 46 are combined with the model of the aortic root representation. Hence, in the combining step 44 a composite image is generated that can then be displayed on a display during the device implantation 46.

The displayed composite image provides the cardiac surgeon or cardiologist with the information needed for a correct deployment of the artificial valve. For actual, respectively current, information it is possible to repeat the fluoroscopy image acquisition 46 in a pre-determined interval. Usually, the fluoroscopy acquisition step 46 is undertaken without the use of contrast agent. By providing the surgeon with the composite image in the display step 46, it is possible to reduce the amount of contrast agent used during the procedure, which means a great relief for patients who have liver problems.

It is also possible to repeat the aortogram acquisition 32 and the following steps for modelling the aortic root representation 36 at a pre-determined rate or according to the actual need, for example, in case a procedure takes longer than actually expected.

Besides using the aortic root representation for the composite image, it is also possible to use this model for measuring, checking and rating the aortic root representation itself in a further checking and exploitation step 50. For example, this can be undertaken on demand or also by automatic measurements 52 providing the surgeon with information that is necessary or that can be used in further treatment or preparation steps.

By combining the aortic root representation with a fluoro acquisition image in the composite step 44 it is possible to provide the surgeon with the most possible amount of information. Amongst others, this is because the information within the fluoro acquisition image is not erased or covered otherwise by simply overlaying pixels from the aortogram on to the fluoro acquisition image. The invention rather provides an aortic root representation where the fluoro acquisition image is nearly fully visible, for example, by showing the aortic root model in a colour that still allows the visibility of the underlying fluoro acquisition image in the composite image.

In a possible embodiment, the aortic root representation can consist of a detected aortic root outline that is manipulated in the further step of modelling, i.e., for example, the root outline is reduced to a one pixel line without interruptions or enclosures. By this manipulation or further preparation of the root outline a model of the aortic root is generated so that within the composite image there is additional information available.

According to the invention, the term of modelling the aortic root representation is understood in a rather broad way, i.e. the modelling may include the above mentioned preparation of the outline, but it can also comprise a more complex modelling such as a rendered or shaded representation of the aortic root to provide the surgeon with an image which provides the impression of a 3-dimensional model. The modelling is, of course, adapted to the fluoro acquisition image which is normally a greyscale or black and white X-ray image. The composite image is adapted for the best visibility and an easy detectability for the surgeon.

Figure 3:
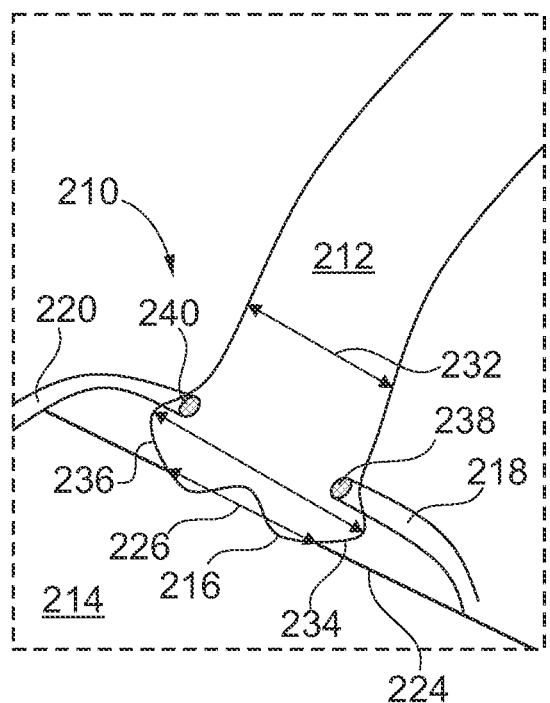
FIG. 3 schematically describes the anatomy of the aortic root.

In FIG. 3 a schematic illustration of an aorta root region 210 is shown, where an aorta 212 is ascending from a heart chamber 214. The aorta is having an annulus 216 at its bottom part providing the connection to the heart chamber 214. Slightly stream upwards from the annulus 216 there is connected to the aorta 212 a left coronary 218 and a right coronary 220. Further, the annulus 216 is shown in relation to its projected plane 224. As FIG. 3 is showing a root diagram according to the invention, there is also indicated an annulus projected diameter 226, a root projected diameter 230 and a projected diameter 232 of the ascending aorta 212. The aorta 212 is also having a so-called left and right sinus 234, 236. The left and right coronaries 218, 220 which are also known as ostia, open into the aorta with openings 238, 240 which should not be blocked with the replacement valve. In other words, the valve is usually located below the openings 238, 240 or its frame features a concave part that avoids the blocking of the coronary artery ostia.

Figure 4:
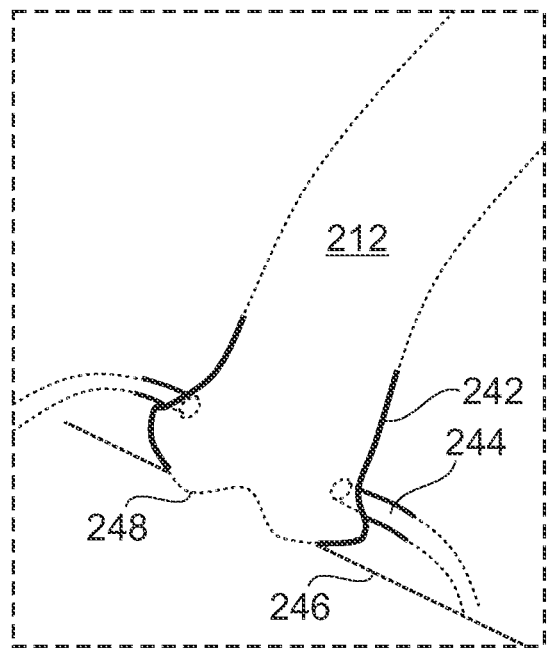
FIG. 4 describes possible elements of the aortic root model.

According to the invention the information shown in the root diagram is processed to provide an aortic root model which is schematically shown in FIG. 4. The aorta 212 is shown with the modelled root outlines 242. The coronaries 216, 220 respectively ostia, are also shown with their modelled outlines 244 only. The modelled annulus plane 224 is shown in a dashed line 246 to indicate that this is only a mere graphical display means. In the area 248 of the annulus 216 where the replacement valve will be deployed, the model is modified such that there is non-intrusive model information in that specific area.

Figure 5A:
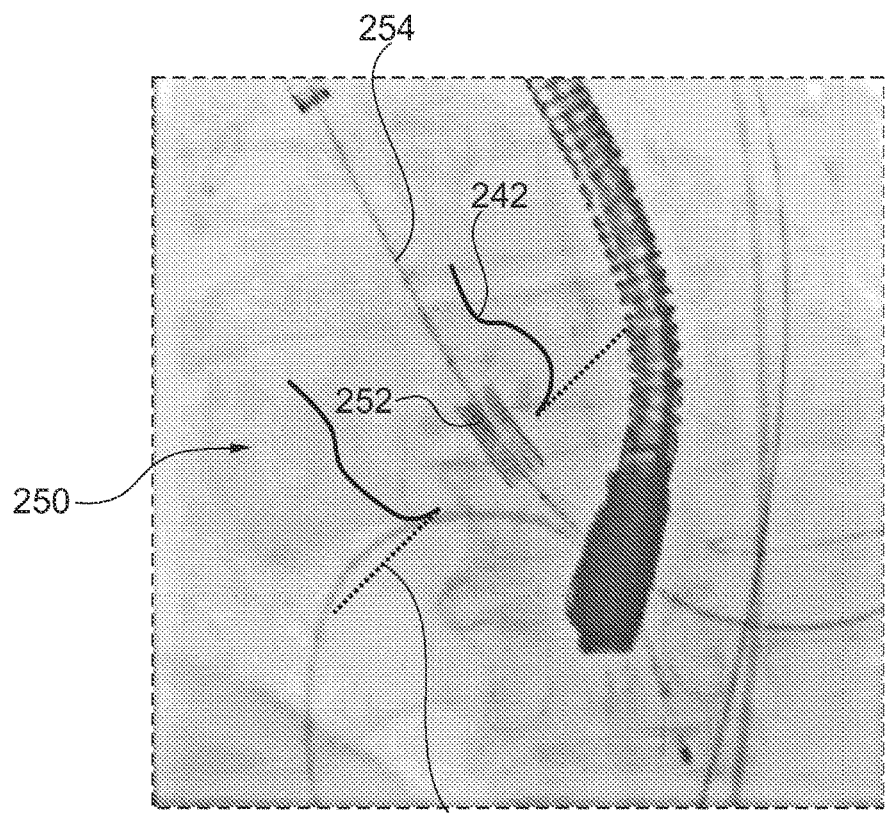
FIG. 5 schematically shows a composite image according to the invention.
Figure 5B:
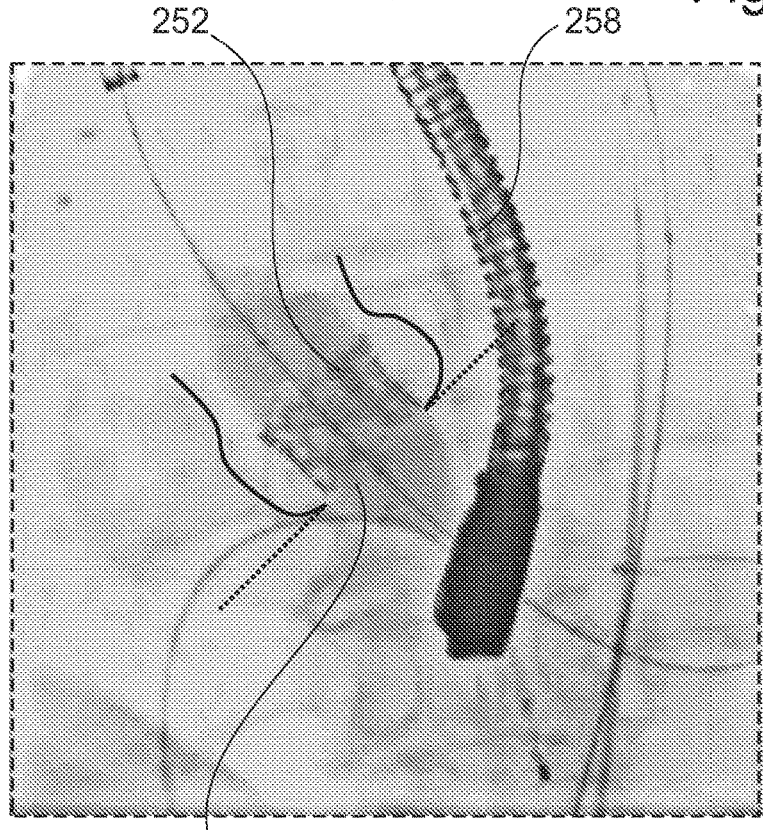

This model is then combined with an X-ray image to form a composite image of which an example is shown in FIGS. 5a and 5b. The aortic root model described in FIG. 4 is computed in an aortagram (not shown). The result is then composed with a fluoroscopy image. In FIG. 5a the composite image is showing an aortic root model 250 which comprises the root outline 242 and the annulus plane 246. A replacement valve 252 with markers is shown in the time of positioning, i.e. the valve 252 is inserted in an unexpended state by the means of a delivery catheter 254. In FIG. 5b the same situation is shown at expansion time. Here, the valve 252 with its base 256 is expended with a balloon. Alternatively self expendable valves can also be used. The composite image according to the invention shows that the device base 256 is well aligned with the annulus plane 246. The dark tube like device 258 is a TEE probe (Trans-Esophagus Echographic) arranged for separate aspects which are not related to the invention.

While the invention has been illustrated and described in details in the drawings and forgoing description, such illustration and description are to be considered illustrative or exemplary and not restrictive; the invention is not limited to the disclosed embodiments.

The invention claimed is:

1. An examination apparatus for providing visual guidance for heart valve replacement, the examination apparatus comprising:
an X-ray image acquisition device;
a display device; and
a processor programmed for:
via use of said image acquisition device and injected contrast agent, acquiring at least one X-ray image of a region of a cardiac vessel root that adjoins a given native valve; and
via said image acquisition device, acquiring a current fluoroscopy image of both said region and of a replacement valve that is for replacing said given native valve and that is disposed within said cardiac vessel,
identifying vessel information data within the at least one acquired X-ray image;
using the identified vessel information data to produce a model including a representation of an outline of said cardiac vessel root and a representation of an annulus plane of said cardiac vessel root;
generating a composite image by merging said model with said current fluoroscopy image overlappingly; and
displaying, via said display device, said composite image, wherein said displaying includes displaying said outline and said representation of said annulus plane.

2. The apparatus according to claim 1, wherein said identifying comprises detecting the vessel root outline of the vessel root region in said at least one acquired X-ray image.

3. The apparatus according to claim 1, wherein said at least one X-ray image comprises a plurality of X-ray images;
wherein the processor is programmed for automatically, without need for user intervention, selecting, from said plurality of X-ray images and for use in said identifying, an image with best contrast.

4. The apparatus according to claim 1, wherein said identifying entails estimating background in said acquired at least one X-ray image, and subtracting the background from said acquired at least one X-ray image by performing a digital subtraction angiography (DSA) procedure.

5. The apparatus according to claim 1, wherein the processor is programmed for, automatically, without need for user intervention, using said model for measuring the vessel root.

6. The apparatus according to claim 1, said image acquisition device comprising a detection module and a radiation source, wherein the processor is connected with both said detection module and said radiation source.

7. The examination apparatus of claim 1, the producing creating, for said displaying, said outline as a one pixel line.

8. The examination apparatus of claim 1, wherein said outline said model comprises is formed by pixels, and wherein said pixels are overlaid onto said current fluoroscopy image such that the overlapping merging does not, in said composite image, cover or erase any pixels of said current fluoroscopy image that adjoin said outline.

9. The examination apparatus of claim 1, wherein said representation in said composite image is shown, via said displaying, in a color that allows visibility of an underlying part of a portion of said current fluoroscopy image relative to a remaining portion of the current fluoroscopy image.

10. The examination apparatus of claim 1, wherein said model comprises an end-product of image manipulation performed automatically, without need for user intervention, on said at least one acquired X-ray image by said examination apparatus so as to reduce an amount of said current fluoroscopy image that is covered, or erased, by the combining of the manipulated image with said current fluoroscopy image.

11. The examination apparatus of claim 1, wherein said model further includes a graphic image that is not an X-ray image including the outline and the representation of the annulus plane, and wherein said generating entails overlaying said graphic image onto said current fluoroscopy image.

12. The examination apparatus of claim 1, wherein said vessel root is an aortic root.

13. The examination apparatus of claim 1, said model including a curve definition, vector data, or both a curve definition and vector data.

14. A catheterization laboratory system comprising the apparatus of claim 6 and further comprising: a table for receiving a subject to be examined; and an interface unit configured for receiving input information from a user.

15. A non-transitory computer readable medium embodying a computer program for providing visual guidance for heart valve replacement, said program having instructions executable by a processor for performing a plurality of acts, said plurality comprising the acts of:
   a) acquiring, with injected contrast agent, an image of a region of a vessel root segment that adjoins a given native valve;
   b) identifying vessel information data within said acquired image;
   c) using the identified vessel information data to model said vessel root, the model including an outline of said vessel root and an annulus plane of the vessel root;
   d) acquiring a current fluoroscopy image of the vessel root region;
   e) generating a composite image by combining the model of said vessel root with said current fluoroscopy image by merging, overlappingly with said current fluoroscopy image, a representation of said model that includes the outline and the representation of the annulus plane; and
   f) displaying said composite image, including the outline and the representation of the annulus plane, on a display.

16. The computer readable medium of claim 15, wherein the acquisition of said current fluoroscopy image in act d) entails acquiring a current fluoroscopy image of a replacement valve that is for replacing said given native valve and that is disposed within said vessel, and wherein said current fluoroscopy image of the replacement valve is combined in forming said composite image to be displayed.

17. The computer readable medium of claim 15, wherein said image of a region of a vessel root comprises an X-ray image of said region.

18. An examination apparatus for providing visual guidance for heart valve replacement, the examination apparatus comprising:
   an X-ray image acquisition device; and a display device;
   said examination apparatus being configured for, via use of said X-ray image acquisition device and injected contrast agent:
      acquiring an X-ray image of a vessel root region of a heart; and
      via said X-ray image acquisition device, acquiring a current fluoroscopy image of both said vessel root region and of a replacement valve that is for replacing a native valve and that is disposed within the vessel,
   said examination apparatus being further configured for:
      identifying vessel information data within the acquired X-ray image;
      producing a model by using the identified vessel information data, the model including an outline of the vessel root region and a representation of an annulus plane;
      generating a composite image by merging said model, overlappingly with said current fluoroscopy image; and
      displaying, via said display device, said composite image,
      wherein said displaying includes displaying said outline and said representation of said annulus plane.

* * * * *